United States Patent [19]
Feng et al.

[11] 4,152,927
[45] May 8, 1979

[54] VISCOSITY SIMULATOR

[75] Inventors: I-Ming Feng, Westfield; Harold Shaub, New Providence, both of N.J.

[73] Assignee: Exxon Research & Engineering Co., Florham Park, N.J.

[21] Appl. No.: 866,373

[22] Filed: Jan. 3, 1978

[51] Int. Cl.² ............................................. G01N 11/14
[52] U.S. Cl. ...................................................... 73/60
[58] Field of Search ...................................... 73/60, 59

[56] References Cited
U.S. PATENT DOCUMENTS
3,350,922  11/1967  Kim et al. ................................. 73/60

FOREIGN PATENT DOCUMENTS
1078351  3/1960  Fed. Rep. of Germany ............... 73/59
464802  8/1975  U.S.S.R. ........................................ 73/59

*Primary Examiner*—Richard C. Queisser
*Assistant Examiner*—Joseph W. Roskos
*Attorney, Agent, or Firm*—F. Donald Paris

[57] ABSTRACT

An improved viscosity measurement device which employs a sample container having a sleeve therein and a rotor disposed within the sleeve. The rotor is cylindrical and includes openings which extend through the rotor in the axial or longitudinal direction, parallel to the rotor axis. This enables the viscometer to test non-Newtonian oils at very low shear rates without introducing non-uniform shear rate.

10 Claims, 2 Drawing Figures

VISCOSITY SIMULATOR

BACKGROUND OF THE INVENTION

The present invention generally related to apparatus for measuring viscosities of oils and more particularly to an improved apparatus for accurately predicting engine cold cranking characteristics, i.e. engine viscosity of a crank case oil.

Generally, the problems associated with accurately predicting cranking characteristics of engine oils in an engine operating at low temperatures, for example below 0° F., are well known. It is also well known that the viscosity of these oils influence the force (i.e. torque required to crank an engine and the engine cranking speed,) and that the viscosity of any oil is temperature dependent. The viscosity of crank case oil influences the ease with which an engine will start at low temperatures.

Those associated with the automotive industry, such an engine manufacturers, oil processors, automobile owners and the like, are extremely interested in being able to determine the viscosity of an engine oil without having to evaluate the oil under controlled conditions in an actual engine. Cranking characteristics of certain categories of non-additive oils such as solvent neutral mineral oils known as "straight mineral" oils can be fairly accurately predicted without actual cranking by using the viscosity at the temperature of interest, for example 0° to 20° F. The viscosity of these oils is obtained by extrapolating low shear viscosities obtained at 100° and 210° F. on the ASTM viscosity temperature chart. However, this procedure is not totally satisfactory for those oils characterized as non-Newtonian which comprise a large majority of the crank case oils presently used. Typical examples of the latter oils are the solvent neutral oils containing viscosity index improvers such as polymethacrylates, often copolymers, polybutenes and styrene polyesters. Use of the extrapolated viscosity technique which can be employed to predict engine cranking characteristics of the "straight mineral" oils are not applicable to non-Newtonian oils.

Heretofore, an instrument which has been used in determining the viscosity of those oils which are not subject to the extrapolated viscosity technique is disclosed in U.S. Pat. No. 3,350,922 assigned to the assignee of the present invention. In that apparatus, a pair of flats are employed on the rotor for permitting air bubbles to escape as the oil is introduced into the annular test space. These flats tend to create a situation of non-uniform shear rates which cannot be tolerated in testing of non-Newtonian oils at very low shear rates, i.e. about 0.05 to about 2 sec.$^{-1}$. The non-uniformity in shear rate has only a very negligible effect on the accuracy of viscosity measurements obtained at high shear rates used in this apparatus, commonly known as a cold cranking simulator. However, most oils at temperatures below 0° F. are highly non-Newtonian, this means that the viscosity of these oils is highly dependent on the shear rate. Wax separation is a common cause of this low temperature Non-Newtonian behavior which is frequently complicated by the polymer-wax interaction. Oils with wax separation show a very steep increase in viscosity with a decrease in shear rate in the low shear rate region. In latter situations the flats provided on the rotor produce extremely large inaccuracies in the measurements obtained because of much lower shear rates inside the flats.

An example of this might be employing a test oil PRO-10 having a viscosity of 885 poises at a shear rate of 2 sec$^{-1}$ and a temperature of −30° F. At the same temperature, and at a shear rate of 1 sec$^{-1}$ the same oil will have a measured viscosity of 1390 poises. Still at the same temperature, but at an even lower shear rate of 0.5 sec$^{-1}$, the viscosity of the same oil reaches 2620 poises. It also has been found that the inaccuracy because of the non-uniform rates introduced by the flats is not a constant error and varies with shear rate and temperature of the non-Newtonian oil undergoing testing. The low-shear-rate viscosity at low temperature is extremely important in its relation to the engine failure due to air binding at the oil pump inlet. Air binding is the result of insufficient oil movement, i.e. insufficient flow at an extremely low shear rate, in the sump for the oil to reach the oil pump inlet because of excessively high oil viscosity at the low shear rate. When air binding occurs, the oil pump picks up only air and sends no oil out to lubricate and engine failure follows quickly.

SUMMARY OF THE INVENTION

The present invention provides an improved rotor design for a low shear rate rotary viscometer which enables the viscometer to function properly and obtain accurate measurements in the testing of non-Newtonian oils at extremely low shear rates and more particularly, without the introduction of a non-uniform shear rate. This is accomplished by providing the cylindrical rotor with at least one opening which extends in the longitudinal direction parallel to the rotor axis. This enables the air contained within the test space to escape as the test sample of oil is introduced into the space. While at least one opening is preferred, a plurality can be provided about the rotor axis. Also, a small number of large openings is preferred to a large number of small openings because the capillary effect in the small openings may impede air escape. An optimum number of openings is in the range from about 1 to 16 and preferably 2 to 8 and most preferably 3 to 4. While the openings are generally circular, they can have other configurations such as an elongated shape fitting the annular space. In the absence of these openings, the air will tend to be trapped in the annular space in the test chamber as the test oil is introduced into the viscometer. Thus, any measurements made by the instrument for viscosity will be for a mixture of oil and air voids and not merely for only oil. While the flats on the rotor of the aforesaid prior art U.S. Pat. No. 3,350,922 permit air bubbles to escape, they also introduce non-uniform shear rates which are undesirable and cannot be tolerated as described above.

DESCRIPTION OF THE PREFERRED EMBODIMENT

Figure 1:
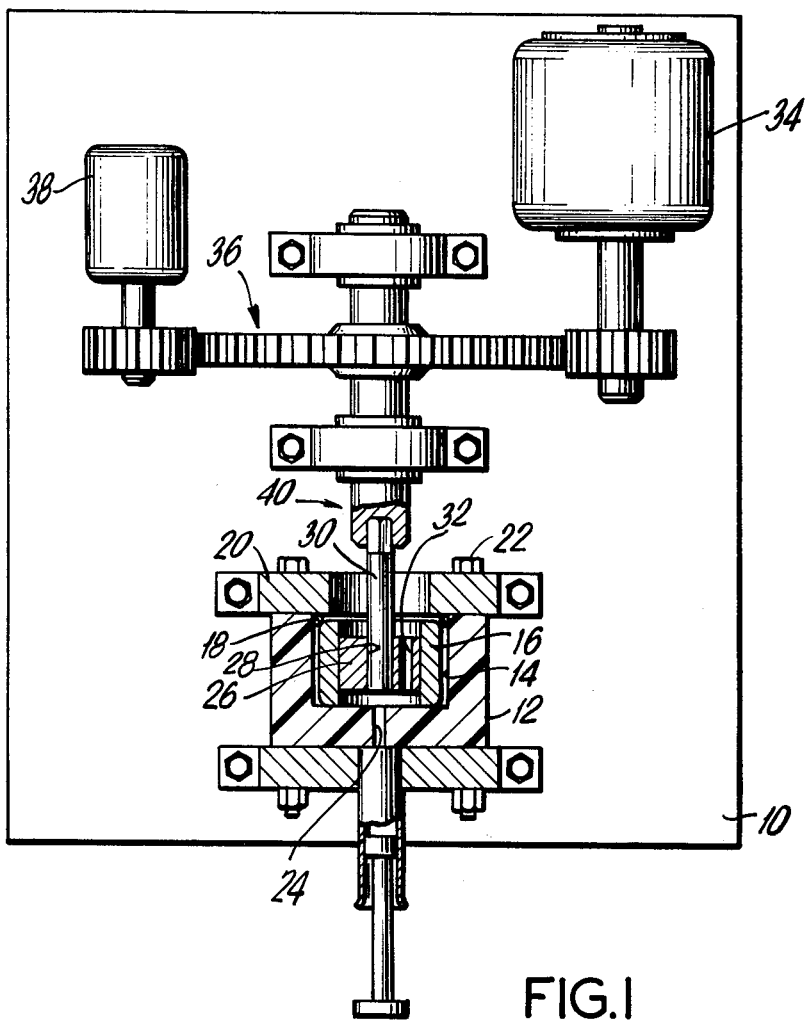
FIG. 1 is an elevational view in partial cross section of an improved engine viscosity simulator according to the present invention.
Figure 2:
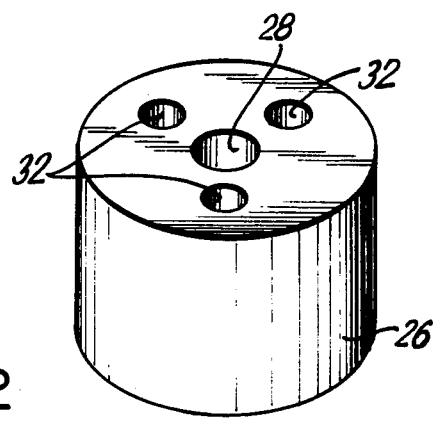
FIG. 2 is a perspective view of the improved cylindrical rotor design employed in the instrument of FIG. 1.

Referring now to the drawings, FIG. 1 in particular, the engine viscosity simulator shown is essentially that disclosed and described in U.S. Pat. No. 3,350,922 which is incorporated herein by reference. Briefly, the instrument which is supported by the structural frame 10 comprises a sample holder 12 having a central generally cylindrical bore or cavity 14. The cavity chamber 14 receives the sleeve 16 which is stationarily held in place by means of the O-rings 18, end-plates 20 and bolts 22. A channel opening 24 is provided in the underside of the holder for insertion of the sample oil which is to be tested. A rotatable drum 26 constructed according to the present invention is snugly fit within the sleeve 16. The drum typically is made from a 0.50 inch length stainless steel cylindrical member which typically has an outside diameter of about 0.750 inch. The drum includes a central opening 28 for mounting it to the shaft 30 and disposed about the central mounting opening 28 are a plurality (three are shown) of elongated axial openings 32. These openings are spaced at approximately 120° apart and are located at a radius of about 0.225 inch. They enable the air contained within the sleeve to escape upwardly as the oil is introduced into the chamber. By maintaining the rotor drum in a cylindrical configuration, i.e. no modification of its outer contour, the uniformity in shear rate is retained and the openings have the additional advantage of reducing the weight of the rotor assembly which lowers the rotational friction encountered. A motor 34 of a conventional type such as disclosed in the aforesaid United States patent is coupled through a gear train generally designated 36 to a tachometer 38 or other suitable rpm measurement instrument and also to a spindle 40 which connects with the shaft 30 and other members described before turning the rotor. The oil to be tested is inserted into the sample holder as explained in the aforesaid patent and although it discloses that instrument may introduce the oil without introducing air bubbles (col. 2, lines 53-54) oftentimes this does not occur because of surface tension and viscous trapping effects. Other features disclosed in that patent, such as the temperature controlling means for maintaining the temperature of the sample being tested substantially constant also can be provided.

What is claimed is:

1. A viscosity simulator for measuring viscosity of liquids, comprising a sample holder including a cavity and a sleeve fixed within said cavity, spindle means operably mounted within said sleeve and comprising in combination a shaft and a drum having bottom and top surfaces, means for driving said spindle means, inlet means spaced from said bottom surface for introducing liquid within said sleeve into a test space between said bottom surface and said inlet means, wherein the improvement comprises:

said drum comprising a cylindrical member having at least an opening extending completely through said member between said top and bottom surfaces thereof substantially parallel to and radially spaced from the axis of rotation of said drum, said opening at said bottom surface being in direct communication with said space, whereby air contained within said space passes through said opening as liquid is introduced into said test space from said inlet means.

2. The simulator of claim 1 wherein said cylindrical member comprises a spaced plurality of said openings extending completely through said member.

3. The simulator of claim 2 wherein said openings are equally spaced in a circumferential direction.

4. The simulator of claim 2 wherein said openings are radially disposed between the main axis of rotation of said member and the periphery of said member.

5. The simulator of claim 1 wherein said member includes three openings.

6. The simulator of claim 2 wherein said openings are of substantially the same size.

7. The simulator of claim 1 wherein each of said openings comprises a circular configuration.

8. The simulator of claim 1 wherein said opening is located substantially midway radially between said main axis and the periphery of said member.

9. The simulator of claim 5 wherein said openings are spaced 120° apart.

10. The simulator of claim 1 wherein said drum fits snugly relative to said sleeve for defining said test space.